United States Patent [19]

Takayama

[11] Patent Number: 4,503,842

[45] Date of Patent: Mar. 12, 1985

[54] ENDOSCOPE APPARATUS WITH ELECTRIC DEFLECTION MECHANISM

[75] Inventor: Syuichi Takayama, Tokyo, Japan

[73] Assignee: Olympus Optical Co., Ltd., Tokyo, Japan

[21] Appl. No.: 438,459

[22] Filed: Nov. 2, 1982

[30] Foreign Application Priority Data

Nov. 4, 1981 [JP] Japan .................. 56-176917

[51] Int. Cl.$^3$ .................. A61B 1/00
[52] U.S. Cl. .................. 128/4; 200/6 A
[58] Field of Search .................. 128/4–8; 200/6 A, 11 K; 318/305, 446

[56] References Cited

U.S. PATENT DOCUMENTS

| 2,507,016 | 5/1950 | Hesh | 200/6 A |
| 3,005,055 | 10/1961 | Mattke | 200/11 K |
| 3,487,179 | 4/1967 | Meier | 200/11 A |
| 3,577,054 | 5/1971 | Banks | 318/305 |
| 4,273,111 | 6/1981 | Tsukaya | 128/6 |
| 4,286,585 | 9/1981 | Ogawa | 128/6 |

FOREIGN PATENT DOCUMENTS

| 2504663 | 8/1976 | Fed. Rep. of Germany | 128/4 |
| 418173 | 8/1974 | U.S.S.R. | 128/6 |

Primary Examiner—Edward M. Coven
Assistant Examiner—Max F. Hindenburg

[57] ABSTRACT

There is disclosed an endoscope apparatus including an electric deflection mechanism which has an insertion section with a deflection portion to be freely deflected, a control section, electric motors, wire drums and angulation wires. A single deflection control lever is arranged in the control section to arbitrarily deflect a distal end portion in any direction. The motors are properly rotated in the forward or reverse direction in accordance with the manual operation of the deflection control lever, thereby properly and very precisely deflecting the deflection portion of the insertion section under the control of the operator through the electric deflection mechanism.

13 Claims, 10 Drawing Figures

ENDOSCOPE APPARATUS WITH ELECTRIC DEFLECTION MECHANISM

BACKGROUND OF THE INVENTION

The present invention relates to an endoscope apparatus and, more particularly, to an endoscope apparatus having an electric deflection mechanism for electrically deflecting an insertion section.

The insertion section of the endoscope is inserted into a body cavity such as a coeliac cavity of a patient and is bent or deflected by an operator, such as a doctor, as needed. An endoscope apparatus is known wherein the insertion section, including a flexible tube, is electrically driven by an electric bending mechanism or electric deflection mechanism in order to improve deflection operability of the insertion section.

The endoscope has an advantage in that the insertion section thereof is directly inserted in the coeliac cavity such as the stomach and intestines for a specific medical purpose. Therefore, the deflection operation of the insertion section of the endoscope in the coeliac cavity must be as precise as possible to guarantee safe endoscopic therapy and to provide technical precision and effectiveness.

According to a conventional endoscope apparatus, in order to deflect the distal end portion of the insertion section which is inserted in a coeliac cavity in a desired direction including four directions (upward, downward, right, and left), at least four deflection control switches which are used to deflect the insertion section in the respective four directions are arranged in the endoscope control section. The operator uses a single switch or a combination of switches among the four switches to deflect the distal end portion of the insertion section in the desired direction.

However, in the conventional endoscope apparatus of the type described above, the switching operation for deflection operation is complex and cumbersome. When the operator, such as a doctor, erroneously presses switches, the insertion section is undesirably deflected in an unexpected direction. Since the insertion section may be deflected too much and/or in an unexpected direction, the distal end portion of the insertion section may touch the tissue of the inner wall of the coeliac cavity. In the worst case, the healthy tissue of the coeliac cavity may be damaged or cut. Since the operability of the control switches for deflecting the insertion section is poor and the rotational frequency of the motor is controlled by the operator, a highly precise and high-speed deflection operation is difficult to perform. As a result, the endoscopic therapy does not sufficiently guarantee technical precision, medical effectiveness, or the safety of the patient.

SUMMARY OF THE INVENTION

It is, therefore, an object of the present invention to provide a new and improved endoscope apparatus wherein easy deflection allows an insertion section of the endoscope apparatus to freely deflect, thereby providing effective therapy and safe endoscopic operation.

An endoscope apparatus in accordance with the present invention comprises an insertion section properly deflected in a coeliac cavity of a body into which the insertion section is inserted, a control section mechanically coupled to the insertion section, a motor device which is provided in the control section and which generates rotational torque used for deflecting the insertion section, a deflection mechanism, and a control device. The deflection mechanism is provided in the insertion section and the control section and is mechanically coupled to the distal end portion of the insertion section and to the motor device. The deflection mechanism suitably deflects the insertion section in accordance with the rotational torque generated by the motor device. The control device includes a single deflection control lever which extends from the insertion section to the outside of the apparatus and is operated to be arbitrarily inclined in any direction with respect to the neutral position thereof. The control device is disposed in the control section and is electrically connected to the motor device therein. Electric power supplied to the device is varied in accordance with a tilt direction of the deflection control lever selected by the operator. The insertion section is then bent or deflected in the desired direction in accordance with the tilt direction of the deflection control lever. Therefore, the distal end portion of the insertion section is arbitrarily and very precisely deflected in the desired direction under the control of the operator who manually operates only the deflection control lever.

BRIEF DESCRIPTION OF THE DRAWINGS

The present invention is best understood by reference to the accompanying drawings, in which.

DETAILED DESCRIPTION OF THE PREFERRED EMBODIMENTS

Figure 1:
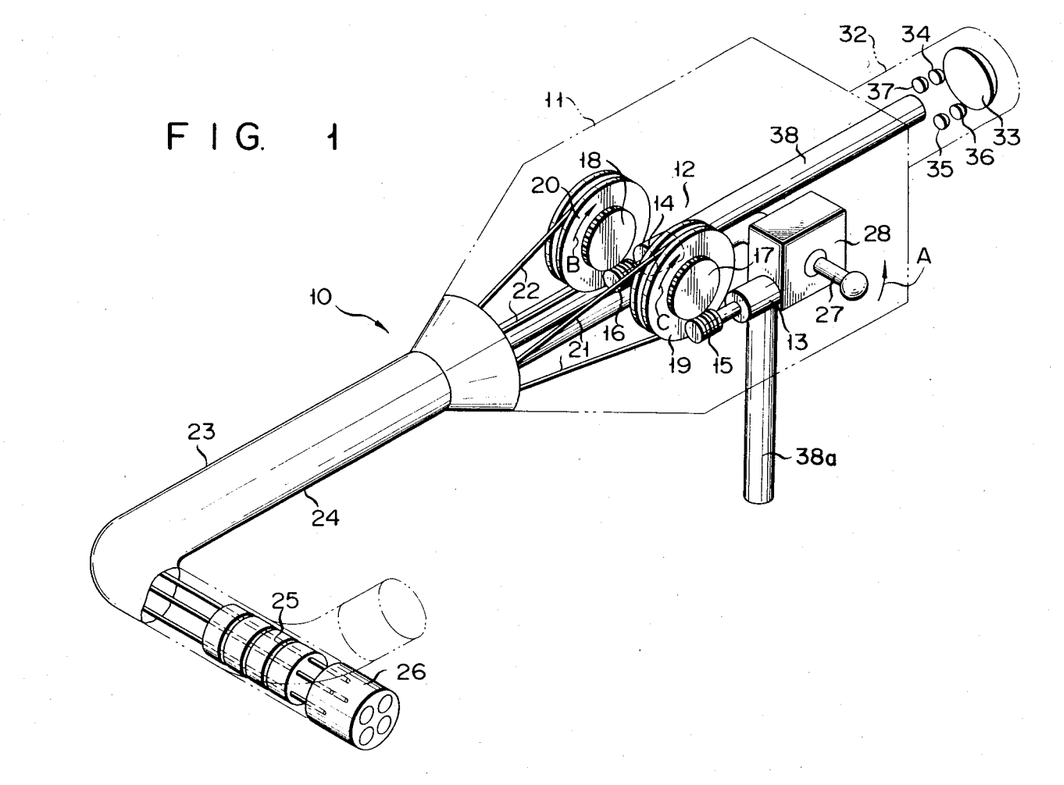
FIG. 1 is a schematic perspective view showing the overall construction of an endoscope apparatus according to a first embodiment of the present invention.

Referring now to FIG. 1, there is illustrated an endoscope apparatus in accordance with the first embodiment of the present invention. An endoscope 10 has a control section 11 which has a motor drive unit or electric deflection mechanism 12 serving as an electric deflection mechanism. Worm gears 15 and 16 are respectively mounted on the rotating shafts of motors 13 and 14 of the motor drive unit 12. Worm wheels 17 and 18 mesh with the worm gears 15 and 16, respectively. The worm wheels 17 and 18 are coaxially mounted on wire drums 19 and 20, respectively. Angulation wires 21 and 22 are wound around the wire drums 19 and 20, respectively. The distal ends of the angulation wires 21 and 22 are secured to a distal end portion 26 of an insertion section 23 through a flexible portion 24 and a deflection portion 25 thereof. In this case, the distal ends of the angulation wires 21 are vertically secured to oppose each other, so that the insertion section 23 can be vertically deflected. The distal ends of the angulation wires 22 are horizontally secured to oppose each other, so that the insertion section 23 can be horizontally deflected.

Figure 2:
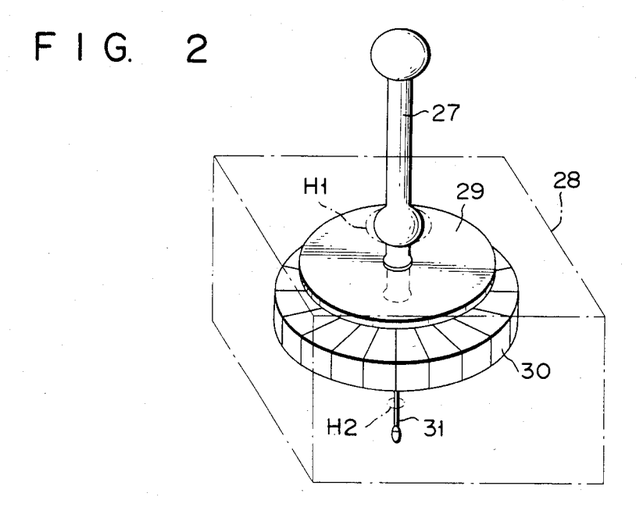
FIG. 2 is a partial perspective view showing the deflection control lever disposed in the endoscope apparatus shown in FIG. 1 in a neutral position.
Figure 3:
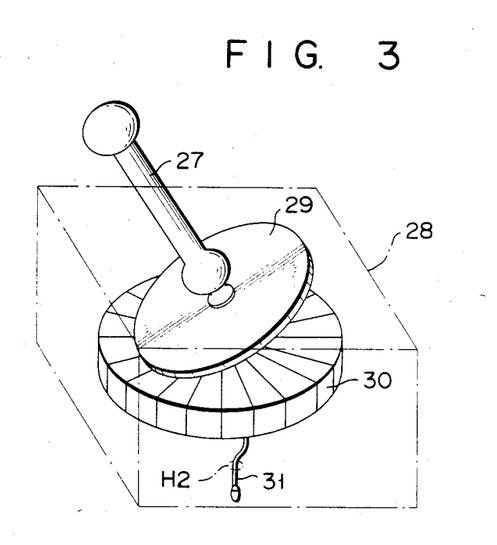
FIG. 3 is a perspective view showing the deflection control section when the deflection control lever shown in FIG. 2 is inclined by the operator.

A single deflection control lever 27 is disposed in the control section 11 to at least partially project outward therefrom and can be manually pivotally inclined by the operator such as a doctor. A switch unit 28 is coupled to the deflection control lever 27, which lever may be pivotally inclined in any direction with respect to the neutral position thereof. As shown in FIG. 2, the switch unit 28 comprises a disc 29 which is coaxially mounted on the deflection control lever 27, and a disc 30 which has 16 contact segments a to p radially disposed thereon. The disc 29 is spaced apart from the disc 30 by a predetermined distance. The deflection control lever 27 is urged by a spring 31 into the neutral position to stand upright when the operator does not apply any force thereto. The deflection control lever 27 is rotated about a fulcrum H1 supported by the switch unit 28. Normally, the spring 31 is disposed in a hole H2 formed in the bottom surface of the switch unit 28 so as to hold the deflection control lever 27 upright. When an external force is applied to the deflection control lever 27 by the operator, the disc 29 is brought into contact with a corresponding contact segment of the disc 30, as shown in FIG. 3. At this time, since one end position of the spring 31 is defined by the hole H2, the spring 31 is elastically deflected and exerts a restoring force to cause the deflection control lever 27 to be restored to the neutral position.

Referring to FIG. 1 again, in an eyepiece section 32 of the endoscope 10 are arranged an ocular lens 33, and light-emitting diodes (LEDs) 34 to 37 which indicate the deflection direction of the deflection portion 25. An image guide 38 which comprises an optical fiber bundle extends from the eyepiece section 32 to the distal end portion 26 of the insertion section 23 through the control section 11. A light guide 38a which also comprises an optical fiber bundle extends from the distal end portion 26 to a universal cord (not shown) through the insertion section 23 and the control section 11, and transmits light obtained from a known endoscope light source apparatus (not shown) from the distal end portion 26 to an external space such as the coeliac cavity.

Figure 4:
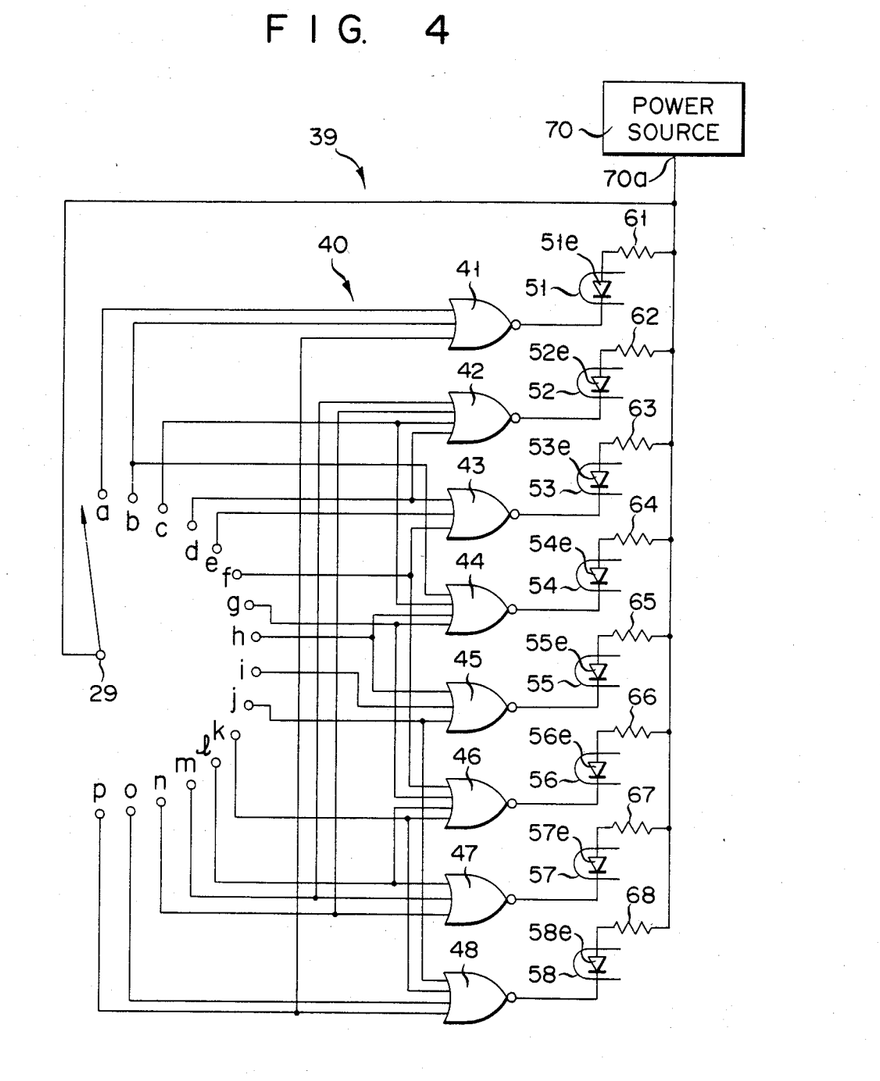
FIG. 4 is a circuit diagram of an electric deflection mechanism of the endoscope apparatus shown in FIG. 1.
Figure 5:
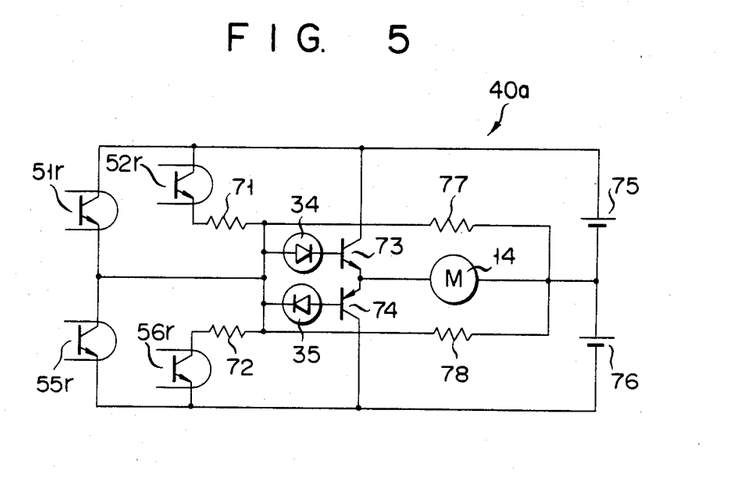
FIG. 5 is a circuit diagram showing a motor as a deflection drive source and its driver circuit.
Figure 6:
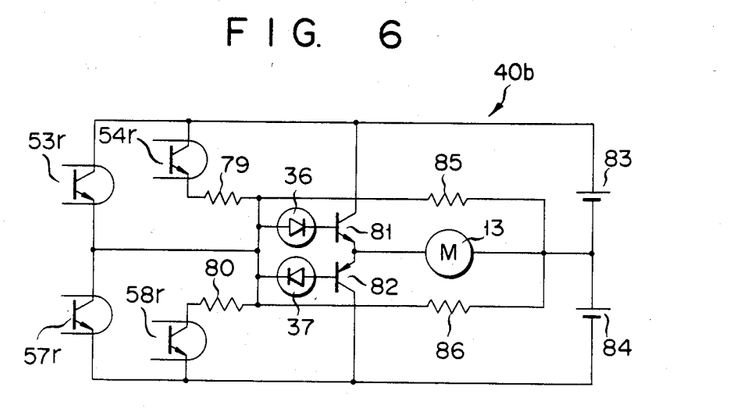
FIG. 6 is a circuit diagram showing another motor as a deflection drive source and its driver circuit.

FIGS. 4 to 6 show an electric circuit 39 of a motor drive unit 12 of the endoscope 10 shown in FIG. 1. The contact segments a to p and gate input ends are electrically connected by means of wiring conductor 40 having a predetermined pattern. Referring to FIG. 4, the three input ends of a 3-input NOR gate 41 are respectively connected to the contact segments a, b and p. The four input ends of a 4-input NOR gate 42 are respectively connected to the contact segments c, d, m and n. The three input ends of a 3-input NOR gate 43 are respectively connected to the contact segments d, e and f. The four input ends of a 4-input NOR gate 44 are respectively connected to the contact segments b, c, g and h. The three input ends of a 3-input NOR gate 45 are respectively connected to the contact segments h, i and j. The four input ends of a 4-input NOR gate 46 are respectively connected to the contact segments f, g, k and l. The three input ends of a 3-input NOR gate 47 are respectively connected to the contact segments l, m and n. Finally, the four input ends of a 4-input NOR gate 48 are respectively connected to the contact segments j, k, o and p. The contact segments a to p are arranged in a semi-circular shape in FIG. 4 only for illustrative convenience. However, in practice, the contact segments a to p are arranged in a circular shape. The input ends of the NOR gates 41 and 48 are also connected to the ground terminal of a power source 70 through respective resistors, but such a connection is not illustrated in FIG. 4. The output ends of the NOR gates 41 to 48 are connected to the cathodes of LEDs 51e to 58e of known photocouplers 51 to 58, respectively. The anodes of the LEDs 51e to 58e are connected to a VCC terminal 70a of the power source 70 through resistors 61 to 68, respectively. The VCC terminal 70a of the power source 70 is connected to the disc 29.

In the motor drive circuit 40a for vertically deflecting the deflection portion 25, as shown in FIG. 5, the collector-emitter paths of phototransistors 51r and 55r of the photocouplers 51 and 55 are respectively connected in series with each other. A node between the collector-emitter paths of the phototransistors 51r and the phototransistor 55r is connected to a node between the anode of the LED 34 and the cathode of the LED 35. The anode of the LED 34 is connected to the emitter of a phototransistor 52r of the photocoupler 52 through a resistor 71. Similarly, the cathode of the LED 35 is connected to the collector of a phototransistor 56r of the photocoupler 56 through a resistor 72. The cathode of the LED 34 and the anode of the LED 35 are connected to the bases of transistors 73 and 74, respectively. A node between the emitters of the transistors 73 and 74 is connected to one end of the motor 14. A node between DC power sources 75 and 76 is connected to the other end of the motor 14. The node between the DC power sources 75 and 76 is connected to the anode of the LED 34 through a resistor 77 and to the cathode of the LED 35 through a resistor 78. The positive terminal of the DC power source 75 is connected to the collectors of the transistor 73 and the phototransistors 51r and 52r. The negative terminal of the DC power source 76 is connected to the collector of the transistor 74 and to the emitters of the phototransistors 55r and 56r.

FIG. 6 shows a motor drive circuit 40b which horizontally deflects the deflection portion 25. This motor drive circuit has substantially the same arrangement as that shown in FIG. 5. Referring to FIG. 6, resistors 79 and 80, transistors 81 and 82, resistors 85 and 86, and DC power sources 83 and 84 correspond to the resistors 71 and 72, the transistors 73 and 74, the resistors 77 and 78, and the DC power sources 75 and 76, respectively.

The mode of operation of the endoscope apparatus according to the first embodiment of the present invention will be described. When the deflection control lever 27 is located in the neutral position, that is, when the operator does not apply any force thereto, the disc 29 does not contact any one of the contact segments a to p. The photocouplers 51 to 58 are OFF, and the motors 13 and 14 are OFF. When the operator moves the deflection control lever 27 in the direction indicated by arrow A in FIG. 1, the disc 29 is brought into contact with the contact segment a. The NOR gate 41 goes low, and the LED 51e of the photocoupler 51 goes on. The phototransistor 51r shown in FIG. 5 is then rendered conductive. A current flows in the base of the transistor 73 through the phototransistor 51r and the LED 34. As a result, the transistor 73 is rendered conductive. The motor 14 is rotated in the forward direction since a current flows through the collector-emitter path of the transistor 73. Upon rotation of the motor 14 in the forward direction, the wire drum 20 is then pivoted in the direction indicated by arrow B. The upper wire of the angulation wires 22 is pulled, and the deflection portion 25 is deflected upward, as shown in FIG. 1. The deflection state is indicated by the LED 34 which is ON. When the deflection portion 25 has been deflected into the desired position, the operator releases the deflection control lever 27. The motor 14 is then stopped and the deflection position of the deflection portion 25 is held in the desired position.

When the operator then operates the deflection control lever 27 to bring the disc 29 into contact with the contact segment c, for example, the NOR gates 42 and 44 in FIG. 4 go low, and the photocouplers 52 and 54 are optically coupled so that the phototransistors 52r and 54r (FIGS. 5 and 6) are rendered conductive. As a result, a bias voltage divided by the resistors 71 and 77 is applied across the transistor 73, while a bias voltage divided by the resistors 79 and 85 is applied across the transistor 81. Drive currents corresponding to these bias voltages flow through the motors 13 and 14, respectively, so that the motors 13 and 14 are rotated at a speed which is half the normal speed. In accordance with the speed of half the normal speed, the wire drums 19 and 20 move relatively slowly in the directions indicated by arrows B and C, respectively. The deflection portion 25 is deflected in the direction corresponding to 45° with respect to the neutral position. This deflection direction can be confirmed when the LEDs 34 and 36 are ON.

The deflection portion 25 of the endoscope 10 can be deflected by repeating the above operation, thereby deflecting the distal end portion 26 in the coeliac cavity in the desired direction. The operator, such as a doctor, operates only the deflection control lever 27 to electrically bring the disc 29 into contact with any one of the contact segments a to p of the disc 30. Thus, the operator can select a desired mode among the predetermined deflection modes. As a result, the deflection portion 25 can be electrically deflected in the desired deflection mode. Since the operator needs to operate only the deflection control lever 27, operability of the endoscope 10 can be greatly improved without requiring a complex switching operation. The distal end portion 26 of the deflection portion 25 of the endoscope 10 can be bent or deflected inside the coeliac cavity in any direction, thereby greatly improving the precision and effectiveness of the endoscopic therapy. Further, since the operator operates only the deflection control lever 27, erroneous deflection operation can be prevented. The deflection portion 25 may not be undesirably deflected too much and/or may not be unexpectedly deflected in a different direction, thus preventing damage to the body of the patient. Furthermore, safe endoscopic therapy is also guaranteed. The deflection direction may be confirmed by means of the LEDs visually disposed in the field of view of the operator as well as by the position of the deflection control lever.

Figure 7:
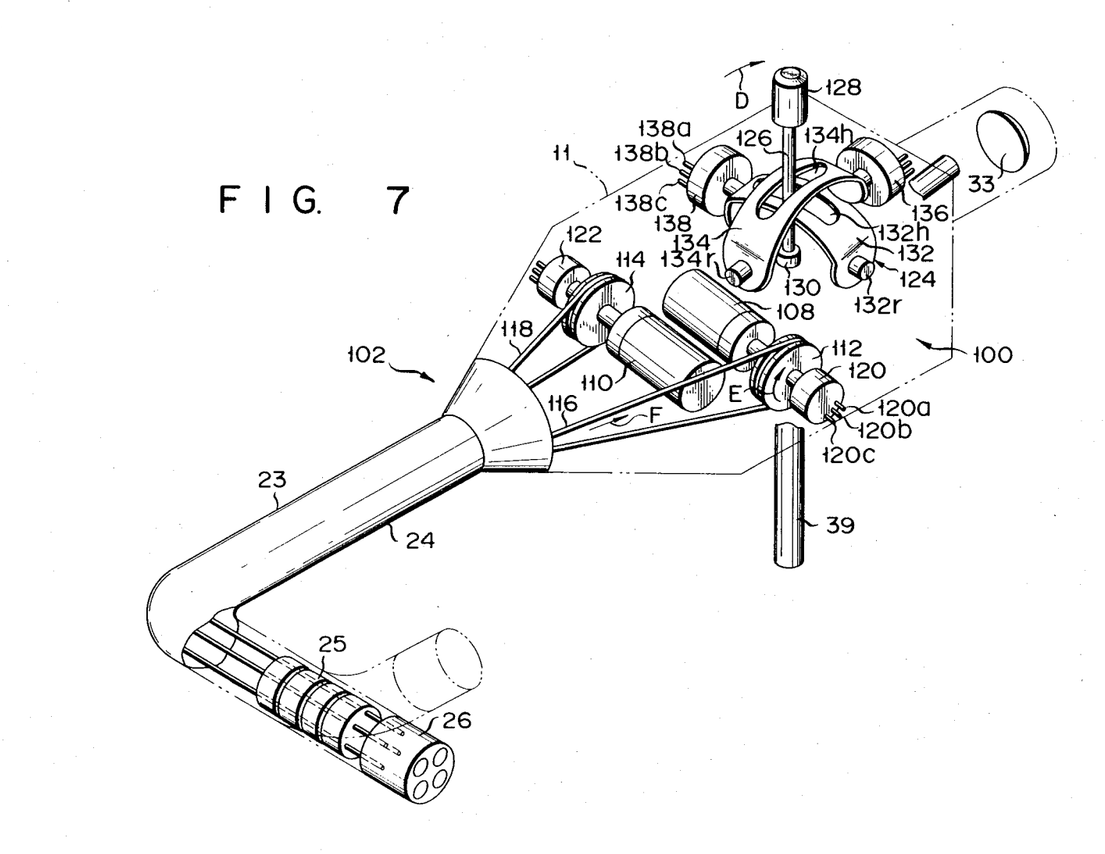
FIG. 7 is a schematic perspective view showing the overall construction of an endoscope apparatus according to a second embodiment of the present invention.
Figure 8:
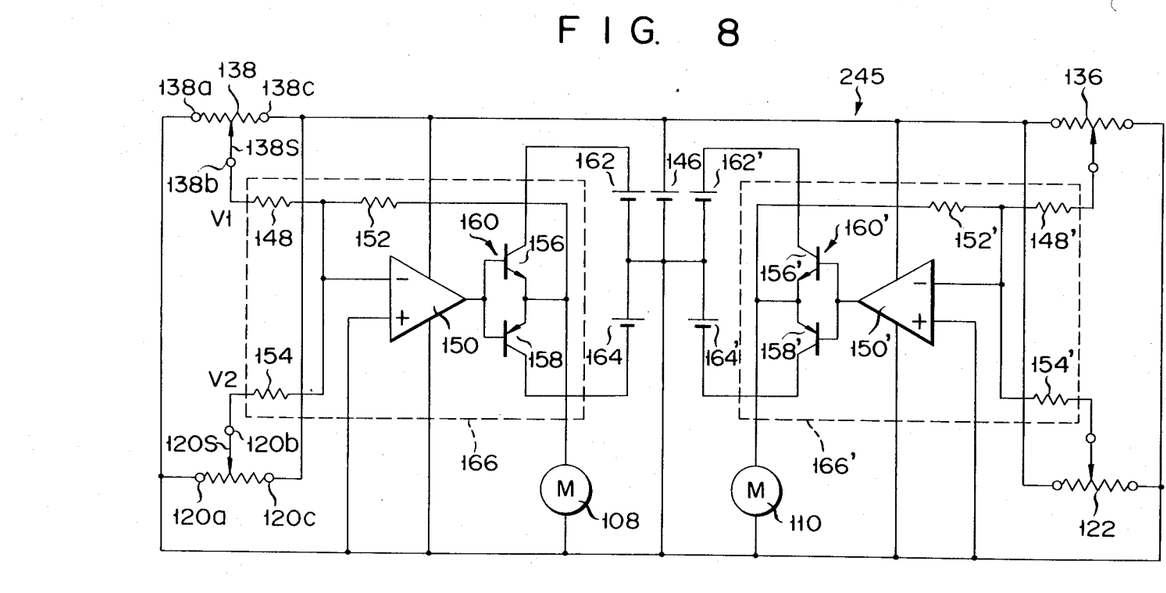
FIG. 8 is a circuit diagram of an electric deflection mechanism of the endoscope apparatus shown in FIG. 7.

FIGS. 7 and 8 show an endoscope apparatus according to a second embodiment of the present invention. The same reference numerals as used in the first embodiment denote the same parts in the second embodiment, and a detailed description thereof will be omitted.

An electric deflection mechanism 100 including two reversible motors 108 and 110 is housed in a control section 11 of an endoscope 102. According to such electric deflection mechanism 100, wire drums 112 and 114 are mounted on the rotating shafts of the motors 108 and 110, respectively. The wire drums 112 and 114 are rotated together with the motors 108 and 110, respectively, in the forward or reverse direction. Angulation wires 116 and 118 are looped around the wire drums 112 and 114, respectively. The angulation wires 116 and 118 extend through an insertion section 23 and the distal ends thereof are secured to a distal end portion 26 in the same manner as in the first embodiment.

Potentiometers 120 and 122 are coaxially mounted to the wire drums 112 and 114, respectively. The potentiometer 120 has terminals 120a, 120b and 120c, and a slidable contact 120s (FIG. 8) which is operated to drive the motor 108 in the forward or reverse direction in a known manner. Therefore, the output voltage of the potentiometer 120 is changed in accordance with movement of the wire drum 112. The potentiometer 122 has the same configuration as the potentiometer 120.

A deflection control mechanism 124 is disposed in the control section 11 to control deflection operation of the endoscope insertion section 23. The deflection control mechanism 124 includes a single deflection control lever 126 which is freely pivotal about its proximal end, and a knob 128 which is attached at the free end of the deflection control lever 126 and extends outside the control section 11 so as to allow the operator to manually operate it. The deflection control lever 126 may be manually inclined in any direction including the forward, backward, right and left directions with respect to the neutral position (the upright position with respect to a fulcrum 130) shown in FIG. 7. The motors 108 and 110 are driven in accordance with the tilt direction and the tilt angle of the deflection control lever 126.

The deflection control lever 126 is mounted at its proximal end on the fulcrum 130 and extends through elongated openings 132h and 134h of pivot frames 132 and 134. The pivot frames 132 and 134 are disposed perpendicularly to each other and are respectively pivotal about shafts 132r and 134r in arc forms in response to movement of the deflection control lever 126 in a known manner. A potentiometer 136 is mounted on the shaft 132r, and a potentiometer 138 is mounted on the shaft 134r. The slidable contacts of the potentiometers 136 and 138 move in synchrony with pivotal movement of the pivot frames 132 and 134 to generate output voltages corresponding to the degree of pivotal movement of the pivot frames 132 and 134, respectively.

FIG. 8 shows the electric circuit 245 which is associated with the deflection operation of the insertion section of the endoscope apparatus according to the second embodiment. The potentiometer 138 is connected between the two terminals of a DC power source 146 through terminals 138a and 138c. The terminal 138b is connected to the first input end of an operational amplifier 150 through a resistor 148 and to the motor 108 through a feedback resistor 152. The potentiometer 120 is connected in parallel with the potentiometer 138. The terminal 120b is connected to the second input end of the operational amplifier 150 through the resistor 154. The output end of the operational amplifier 150 is connected to a node between the bases of npn and pnp transistors 156 and 158 which together constitute a current amplifier 160. The emitters of the transistors 156 and 158 are connected together, and the node thereof is connected to the motor 108. Two DC power sources 162 and 164 are connected between the collectors of the transistors 156 and 158. The operational amplifier 150 and the current amplifier 160 which comprises the transistors 156 and 158 constitute a servo control circuit 166.

The motor 110, and the deflection control circuit including the motor 110 and the pivot frame 134, have substantially similar configurations as above, and a detailed description thereof will be omitted to prevent redundancy of the present specification. In order to correspond circuit elements of the servo control circuit 166 to circuit elements of a servo control circuit including the motor 110, the circuit elements of the latter are indicated by corresponding reference numerals having a dash or prime.

The mode of operation of the endoscope apparatus according to the second embodiment will be described hereinafter. When the operator moves the deflection control lever 126 in the direction indicated by arrow D in FIG. 7, the pivot frame 132 is urged by the deflection control lever 126 and is moved in the direction indicated by arrow D. At the same time, a slidable contact 138s of the potentiometer 138 is moved toward the terminal 138c in accordance with the degree of movement of the pivot frame 132. Therefore, a terminal voltage V1 at the terminal 138b is increased and is higher than a terminal voltage V2 at the terminal 120b of the potentiometer 120. As a result, a negative voltage appears at the output end of the operational amplifier 150, and the transistor 158 is rendered conductive. A voltage proportional to the output voltage from the operational amplifier 150 is applied across the motor 108 which is then driven. The wire drum 112 is rotated in the direction indicated by arrow E in FIG. 7, and the upper wire of the angulation wires 116 is pulled in the direction indicated by arrow F. The distal end of the upper wire which is located in the distal end portion 26 is pulled. As a result, the deflection portion 25 of the insertion section 23 is deflected upward. At this time, the slidable contact 120s of the potentiometer 120 coaxially disposed with the wire drum 112 of the motor 108 is moved toward the terminal 120c. Thus, the terminal voltage V2 (FIG. 8) at the terminal 120b is also increased.

When the terminal voltage V2 at the terminal 120b becomes substantially equal to the terminal voltage V1, the output voltage from the operational amplifier 150 is set at substantially 0 V. The transistor 158 is turned OFF, and the motor 108 is stopped. In this manner, the terminal voltage V1 of the potentiometer 138 disposed in the deflection control mechanism 124 is changed in accordance with the degree of movement of the deflection control lever 126. The motor 108 is also driven in accordance with the degree of movement described above. At this time, the potentiometer 120 is synchronous with the motor 108 and changes its terminal voltage V2 in accordance with the rotating action of the motor 108. When a difference between the terminal voltages V1 and V2 becomes substantially zero, the motor 108 is immediately stopped.

In the second embodiment described above, the operator operates only the deflection control lever 126 to electrically deflect the deflection portion 25 of the insertion section 23 in the desired direction. Therefore, the operability of the endoscope concerning the deflection operation can be greatly improved, and endoscopic therapy of the coeliac cavity is effectively performed. Furthermore, since the deflection portion 25 can be very precisely deflected in accordance with the electrically detected degree of movement of the deflection control lever 126, the deflection portion will not overrun, thus providing safer endoscopic operation.

Although the present invention has been shown and described with respect to particular embodiments, nevertheless, various changes and modifications which are obvious to a person skilled in the art to which the invention pertains are deemed to lie within the spirit, scope and contemplation of the invention.

In the second embodiment, the degree of movement of the deflection control lever is detected by electrically processing output voltages from the potentiometers in the servo control circuit which includes the operational amplifier. However, the electrical detection technique of the degree of movement of the deflection control lever need not be limited to the above technique. The detection technique may vary in accordance with the technical level of the person skilled in the art.

Figure 9:
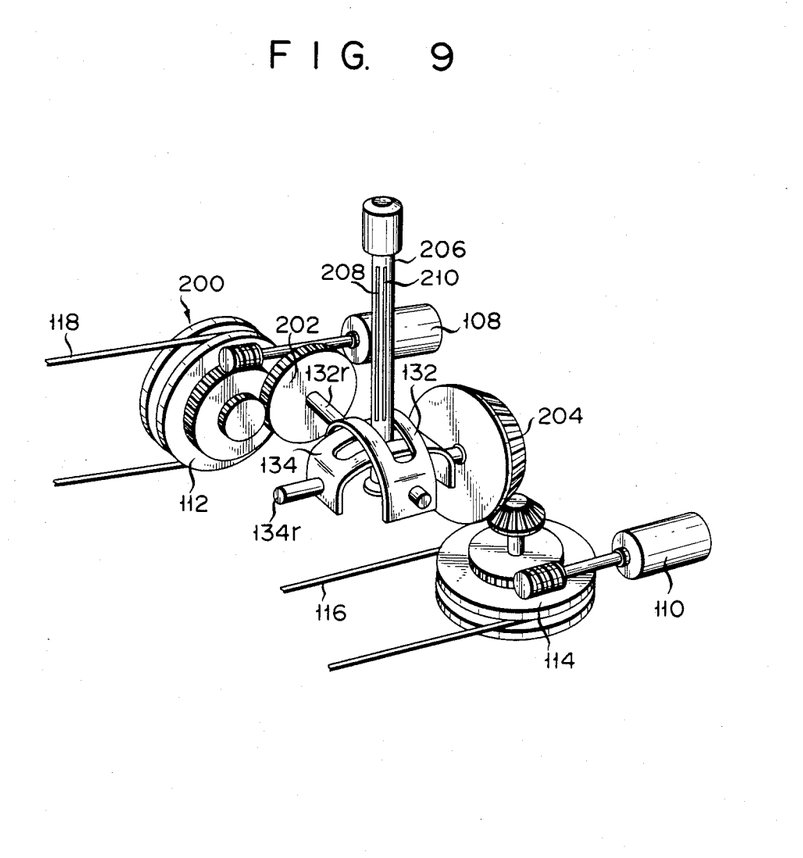
FIG. 9 is a partial perspective view schematically showing a modification of the main part of the electric deflection mechanism.
Figure 10:
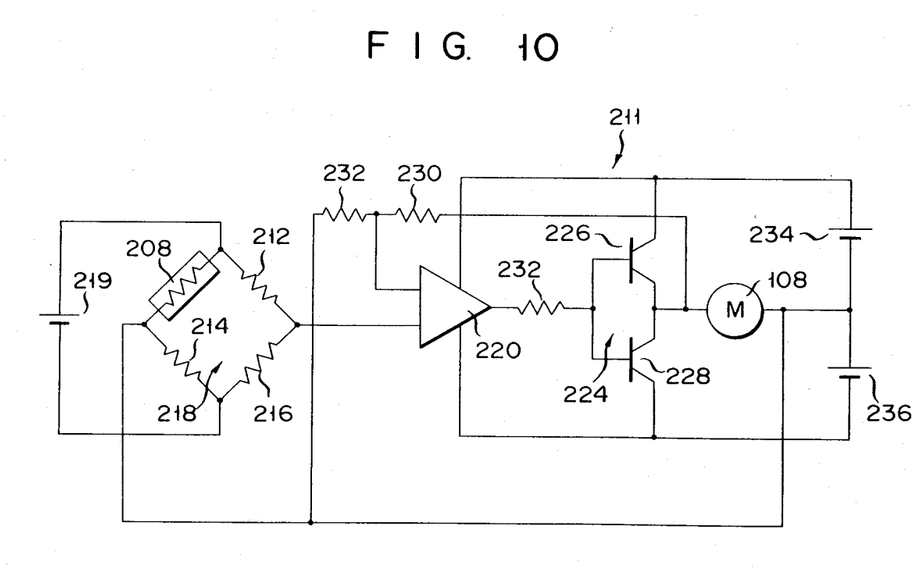
FIG. 10 is a circuit diagram of the electric deflection mechanism shown in FIG. 9.

FIGS. 9 and 10 show a modification for detecting the degree of movement of the deflection control lever, wherein pressure-sensitive elements such as piezoelectric rubber portions are adhered to two surfaces of an elastic deflection control lever so as to detect a distortion of the lever on the basis of the outputs from the pressure-sensitive elements.

In an electric deflection mechanism 200 shown in FIG. 9, spur gears 202 and 204 are respectively mounted on shafts 132r and 134r of pivot frames 132 and 134. The spur gears 202 and 204 are mechanically coupled to the wire drums 112 and 114 which are synchronously driven with the motors 108 and 110 through known gear mechanisms. Resistor distortion gauges 208 and 210 which comprise two piezoelectric rubber portions are adhered to the surface of a deflection control lever 206 which comprises an elastic material. The distortion gauges 208 and 210 change their resistances when a compression or tensile force is applied thereto.

FIG. 10 is a circuit diagram of a deflection drive circuit 211 of the modification (FIG. 9) which includes the distortion gauge 208, to vertically deflect the deflection portion 25. A circuit configuration of a deflection drive circuit which horizontally deflects the deflection portion 25 and which includes the distortion gauge 208 is substantially the same as the deflection drive circuit 211, and a detailed description thereof will be omitted. Referring to FIG. 10, the resistor distortion gauge 208, together with three resistors 212, 214 and 216, constitutes a bridge circuit 218. A DC power source 219 is connected between the input ends of the bridge circuit 218. One other output end of the bridge circuit 218 is connected to one input end of a differential amplifier 220. The output end of the bridge circuit 218 is connected to the first terminal of the motor 108. The output end of the differential amplifier 220 is connected, through the resistor 222, to a buffer circuit 224 which comprises transistors 226 and 228 connected in series with each other. A common node between the emitters of the transistors 226 and 228 is connected to the second terminal of the motor 108, to the other input end of the differential amplifier 220 through a resistor 230, and to the other output end of the bridge circuit 218 through the resistor 230 and a resistor 232. Reference numerals 234 and 236 denote DC power sources, respectively.

In the modification having the configuration described above, when the deflection control lever 206 is not deflected, the bridge circuit 218 is balanced. Therefore, the output voltage from the bridge circuit 218 is zero.

When the operator deflects the deflection control lever 206, a compression or tensile stress is applied to the distortion gauge 208. The resistance of the distortion gauge 208 is changed in accordance with the compression or tensile stress. As a result, a potential difference which corresponds to a change in resistance of the distortion gauge 208 appears between the output ends of the bridge circuit 218. The buffer circuit 224 causes the motor 108 to be driven in the forward or reverse direction in accordance with the potential difference described above, thereby deflecting the deflection portion of the endoscope.

When the wire drum 112 is rotated upon deflection of the deflection portion of the endoscope, the spur gear 202 which meshes with the wire drum 112 is rotated. Upon rotation of the gear 202, the pivot frame 132 is gradually pivoted so as to push the deflection control lever 206 to eliminate deflection of the deflection control lever 206. Therefore, unless the operator applies further force to the deflection control lever 206, the deflection of the deflection control lever 206 itself is automatically released. At this time, the bridge circuit 218 is returned to the balanced state since no external force is applied, and the output voltage from the bridge circuit 218 becomes zero. The transistors 226 and 228 which constitute the buffer circuit 224 are turned OFF, and the motor 108 is automatically stopped. In this manner, the operator operates only the deflection control lever 206 to electrically deflect the deflection portion of the endoscope. The deflection operability of the endoscope is greatly improved in the same manner as in the first and second embodiments, thereby providing safe and efficient endoscopic therapy. Further, since the degree of actual movement of the deflection control lever 206 is electrically detected by the bridge circuit 218 which includes the distortion gauges so as to deflect the deflection portion in accordance with detected data, highly precise deflection operation can be performed. The distal end portion of the insertion section may not unexpectedly abut against the tissue of the coeliac cavity, thus providing safe endoscopic therapy.

In the first embodiment shown in FIGS. 1 to 6, the sixteen contact segments are radially disposed. However, the number of contact segments is not limited to sixteen, but may be more or less than sixteen. Furthermore, microswitches may be used in place of the contact segments.

What is claimed is:

1. An endoscope apparatus comprising:
   (a) an insertion section adapted to be deflective in a coeliac cavity of a living body into which said insertion section is inserted;
   (b) a control section mechanically coupled to said insertion section;
   (c) first motor means provided in said control section for generating rotational torque to bend said insertion section in a first direction;
   (d) second motor means provided in said control section for generating rotational torque to bend said insertion section in a second direction;
   (e) a deflection means, provided in said control section and said insertion section and mechanically coupled to a distal end of said insertion section and to said first and second motor means, for deflecting said insertion section in accordance with the rotational torques generated by said first and second motor means; and
   (f) control circuit means including a single deflection control lever arranged in said control section and electrically connected to said first and second motor means for varying the amount of power to be supplied to said first and second motor means in accordance with manual inclination of said control lever by an operator and for selectively supplying power to said first motor means, said second motor means or to both said first and second motor means to drive said first and second motor means when said control lever is inclined in a predetermined direction, thereby allowing said distal end of said insertion section to directly deflect in an aimed direction, said deflection control lever being disposed to at least partially extend from said control section to the outside thereof and being pivotally inclinable in any direction with respect to a neutral position thereof.

2. An apparatus according to claim 1, wherein said control circuit means independently varies amounts of power supplied to said first and second motor means in response to the inclination of said deflection control lever to thereby change the rotational torques generated by said first and second motor means, whereby manual operation of said deflection control lever causes said distal end of said insertion section to deflect in any of three directions.

3. An apparatus according to claim 2, wherein said control circuit means comprises:
   detecting means for electrically detecting the inclined direction of said deflection control lever and for producing a detection signal; and
   motor drive circuit means electrically connected to said detecting means, for determining a deflection operation mode of said insertion section in response to the detection signal and for supplying to said first and second motor means that amount of power which is necessary for directing said distal end of said insertion section in a selected third direction in accordance with said deflection operation mode.

4. An apparatus according to claim 3, wherein said first and second motor means respectively comprises first and second reversible electric motors which rotate in a forward and a reverse direction in accordance with power supplied thereto, thereby allowing said distal end of said insertion section to be directed in any one of a plurality of radial directions including first, ssecond and third directions with respect to a reference position of said insertion section, which is defined by the position of said insertion section when said insertion section is undeflected.

5. An apparatus according to claim 4, wherein said motor drive circuit means includes two motor drive circuit sections for driving said first and second reversible electric motors independently of each other by separately changing power supplied to said reversible electric motors in accordance with the deflection operation mode.

6. An apparatus according to claim 5, wherein said motor drive circuit means further includes:
   deflection operation mode determination circuit means electrically connected to said detecting means and said motor drive circuit sections, for storing a plurality of predetermined deflection operating modes for said insertion section, for selecting a specific deflection operating mode among said plurality of predetermined deflection operating modes, and for supplying a deflection control signal corresponding to the specific deflection operating mode to said motor drive circuit sections.

7. An apparatus according to claim 6, wherein said detecting means includes a detection switch circuit having a plurality of switch output terminals and a slider movable in cooperation with said deflection control lever and which electrically contacts one of said plurality of switch output terminals when said deflection control lever is inclined; and said deflection operating mode determination circuit means includes a plurality of logic gates each of which has an output end connected to said motor drive circuit sections and each of which has a plurality of input ends, and wiring conductor means having a predetermined pattern for electrically connecting said plurality of input ends of each of said logic gates to said plurality of switch output terminals.

8. An apparatus according to claim 3, wherein said detecting means includes potentiometer means having a slider movable in cooperation with said deflection control lever, for producing a detection signal as an output voltage which corresponds to the degree of movement of said deflection control lever deflected by the operator.

9. An apparatus according to claim 8, wherein said motor drive circuit means includes:

switch circuit means connected to said motor means, for performing a switching operation; and switch circuit controlling means connected between said potentiometer means and said switch circuit means, for controlling the switching operation of said switch circuit means in response to the output voltage from said potentiometer means, thereby changing a current flowing to said motor means.

10. An apparatus according to claim 9, wherein said motor means includes reversible electric motors, and said switch circuit means includes switch circuits which respectively correspond to said reversible electric motors and which change currents flowing to said reversible electric motors.

11. An apparatus according to claim 1, wherein said detecting means includes:

pressure-sensitive means adhered to said deflection control lever, for changing an electrical resistance thereof in accordance with a mechanical distortion when said deflection control lever is deflected; and bridge circuit means electrically connected to said pressure-sensitive means, for producing a detection signal in accordance with a change in the electrical resistance of said pressure-sensitive means.

12. An apparatus according to claim 11, wherein said motor drive circuit means includes:

switch circuit means connected to said motor means, for changing a current flowing to said motor means by a switching operation; and switch circuit controlling means connected between said bridge circuit means and said switch circuit means, for controlling the switching operation of said switching circuit means in response to the detection signal from said bridge circuit means.

13. An apparatus according to claim 12, wherein said deflection control lever comprises an elastic material at least at a portion where said pressure-sensitive means is disposed.

* * * * *